(12) United States Patent
Gruber

(10) Patent No.: US 6,171,617 B1
(45) Date of Patent: Jan. 9, 2001

(54) EFFERVESCENT IBUPROFEN PREPARATION AND PROCESS FOR THE PRODUCTION THEREOF

(75) Inventor: Peter Gruber, Bottmingen (CH)

(73) Assignee: Losan Pharma GmbH, Neuenburg (DE)

(*) Notice: Under 35 U.S.C. 154(b), the term of this patent shall be extended for 0 days.

(21) Appl. No.: 09/125,210

(22) PCT Filed: Feb. 19, 1997

(86) PCT No.: PCT/EP97/00789

§ 371 Date: Jan. 6, 1999

§ 102(e) Date: Jan. 6, 1999

(87) PCT Pub. No.: WO97/30698

PCT Pub. Date: Aug. 28, 1997

(30) Foreign Application Priority Data

Feb. 20, 1996 (DE) ................................. 196 06 151

(51) Int. Cl.[7] ................................. A61K 9/14; A61K 9/46
(52) U.S. Cl. ................................. 424/466; 424/489; 514/784; 514/951
(58) Field of Search ................................. 424/465, 466, 424/489, 451, 456

(56) References Cited

U.S. PATENT DOCUMENTS

| 3,882,228 | 5/1975 | Boncey et al. ................ 424/489 |
| 4,414,198 | 11/1983 | Michaelson ................. 424/44 |
| 4,832,956 | 5/1989 | Gergely et al. ................ 424/466 |

FOREIGN PATENT DOCUMENTS

| 0 181 564 A1 | 11/1984 | (EP). |
| 0 203 768 A2 | 5/1986 | (EP). |
| 0 351 353 A1 | 7/1988 | (EP). |
| 0 667 149 A1 | 2/1994 | (EP). |
| 2 698 788 A1 | 12/1992 | (FR). |
| 91/07174 | 11/1990 | (WO). |

*Primary Examiner*—James M. Spear
(74) *Attorney, Agent, or Firm*—Standley & Gilcrest LLP

(57) ABSTRACT

In particular, the invention relates to a new, clearly dissolving ibuprofen effervescent formulation and a process for the preparation of this formulation.

Ibuprofen or (±)2-(4-isobutylphenyl)-propionic acid has the following structural formula

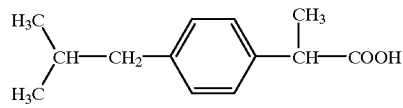

and has been for years a proven, non-steroidal antiphlogistic from the group of phenylpropionic acid derivatives, which shows effectiveness in veterinary experimental inflammation models by inhibiting prostaglandin synthesis.

20 Claims, No Drawings

EFFERVESCENT IBUPROFEN PREPARATION AND PROCESS FOR THE PRODUCTION THEREOF

This application is a 371 of PCT/EP97/00789 filed Feb. 19, 1997.

The invention relates to the subject matter stated in the claims.

In particular, the invention relates to a new, clearly dissolving ibuprofen effervescent formulation and a process for the preparation of this formulation.

Ibuprofen or (±)2-(4-isobutylphenyl)-propionic acid has the following structural formula

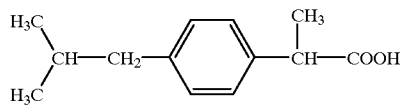

and has been for years a proven, non-steroidal antiphlogistic from the group of phenylpropionic acid derivatives, which shows effectiveness in veterinary experimental inflammation models by inhibiting prostaglandin synthesis. In human therapy, ibuprofen reduces pain caused by inflammation, swellings and fever. It shows the undesired side-effects typical for non-steroidal antirheumatics.

The pharmacokinetic properties of the substance are well-studied. Several clinical studies have also indicated that the start and the intensity of the analgetic effects correlate to the plasma-ibuprofen-concentration. In the case of ibuprofen, Laska et al. have shown that particularly in the first two hours after application, an increased plasma-ibuprofen level results in an increased analgetic effect. Another study has shown that soluble ibuprofen starts to relieve pain earlier than ibuprofen tablets. In the case of ibuprofen, it is also evident that the galenic formulation exerts a great influence on the adsorption rate and on the start of the analgetic effect. Several studies have also shown that effective ibuprofen-plasma levels appear significantly earlier with ibuprofen-lysinate compared to ibuprofen acid (G. Geisslinger et al. in Drug Invest. 5 (4), 238–242 (1994).

As can be seen from the above structural formula, ibuprofen has an asymmetrical carbon atom and is present as the racemate in the therapeutically used form. As is known for several drug agents having one or more asymmetrical carbon atoms, one of the enantiomeric forms is often far more effective than the other. It is known that R-(−)ibuprofen is essentially less pharmacologically active than S-(+)ibuprofen. It was established, however, that the S(+)-form of ibuprofen has an essentially greater pharmacologic potential in the absence of the R(−)-form as had been hypothesized (cf. DE-OS 36 39 038).

However, drugs for pain-relief should have reasonable prices. At the moment, there is the situation that water soluble salts such as ibuprofen-lysinate and ibuprofen-sodium are far more expensive than ibuprofen acid itself and other widely used analgetics such as aspirin and paracetamol.

Thus, great efforts have been made to formulate ibuprofen galenically in such a way that the cheap ibuprofen acid dissolves rapidly and completely. However, these efforts have ended in failure until now. Ibuprofen is an organic acid having a poor solubility. Only just at a pH-value of about 7 does the acid form a salt whereby the solubility is increased significantly (pK-value of ibuprofen acid: 4.5). Because of the immense circulation of ibuprofen it would be substantially helpful if ibuprofen acid could be made to dissolve more rapidly and less pH-dependently by the skillful choice of adjuvants and without complicating the preparation of the drugs. This becomes more important since ibuprofen has a low melting point and can only be processed with difficulty.

The taste of ibuprofen acid is bad and remains for a long period of time in the mucous membranes which are irritated by the active ingredient. Therefore, all solid forms of ibuprofen have to be processed into film tablets or in several cases even into dragees in order to avoid the bad taste during swallowing. Of course, this leads to a further extension of the disintegration and dissolution of the active ingredient.

EP-A-0 228 164 (Boots) describes an ibuprofen effervescent formulation giving rise to a suspension of ibuprofen after decrease of the effervescent reaction. The resulting suspension contains the active ingredient in form of fine particles which stick partially on the mucous membrane of the oral cavity after drinking and lead to burning and local irritations after swallowing of the solution.

DE-A-36 38 414 discloses the addition of arginine or lysine in an amount exceeding the molar level to obtain a soluble form of ibuprofen. The addition of these amino-acid-components causes great disadvantages. Arginine and lysine are very expensive for use as a pharmaceutical adjuvant and exceed by far the costs of the active ingredient ibuprofen itself. The effervescent part contains sodium hydrogen tartrate as an acid component. Sodium hydrogen tartrate exerts such a poor acidic effect that the intensity of the effervescent reaction at a pH-value at above 6.5 for the complete system is low. Therefore, the typical appropriate effervescent effect expected by the patient is not achieved.

EP-A-203 768 discloses an effervescent composition, which can contain paracetamol, acetylsalicyl acid or ibuprofen. It is therein proposed to granulate the active ingredient with an adjuvant for granulation (e.g. PVP) wherein the granules are mixed together with a part of a component of the effervescent mixture, then mixing this pre-mixture together with an effervescent system. The described procedure is suitable for the preparation of clearly soluble effervescent formulations of paracetamol and aspirin, however, not ibuprofen. According to this procedure, 200 mg ibuprofen containing effervescent formulations which dissolve in 150 ml water at about 20° C. within 2 minutes to give more than 90% dissolved ibuprofen cannot be prepared. In order to achieve this in general, the ibuprofen would have had to have been granulated together with basic adjuvants. Otherwise the ibuprofen is dispersed undissolved in the effervescent tablet solution, but which is, however, not desired.

EP-B-0 351 353 discloses ibuprofen effervescent tablets wherein the active ingredient is prepared in combination with sodium hydrogen carbonate and citric acid. Sodium hydrogen carbonate is used excessively to increase the solubility of ibuprofen. There are great doubts as to whether effervescent solutions are formed by this simple composition in which the active ingredient is completely dissolved within the usual time of a few minutes. All practical experiences have shown that dissolved ibuprofen in the form of its salt is again precipitated by the relative strong citric acid. The precipitated ibuprofen rises to the water surface in the form of small oil droplets, gathers together and crystallizes gradually in form of coarse crystals which redissolve again very slowly. The process described in EP-A-0 351 353 has been well-known for years. Acetylsalicylic acid, for example, is prepared as effervescent tablets by adding sodium hydrogen carbonate to the effervescent composition in order to enhance the dissolution of the organic ASS-acid.

EP-A-369 228 (Bayer) discloses an ibuprofen effervescent preparation with the following composition:

1 part by weight of a water soluble ibuprofen salt,
2–10 parts by weight of a excipient,
0.3–0.8 parts of weight of a stabilizer,
0.1–1 parts by weight of sodium carbonate or potassium carbonate.

The Bayer process for the preparation of the aforementioned preparation is extremely expensive since the water soluble ibuprofen salt has to be first of all processed into a clear solution by PVP and a great amount of water. This clear solution is sprayed onto sodium hydrogen carbonate in a fluidized bed granulator. These granules are then sprayed with sodium carbonate, which is dissolved again in a great amount of water. When these granules are processed into effervescent tablets, they should be sprayed once more with an aqueous disodium fumarate solution according to EP-A-0 369 228. These steps are very expensive and require spraying at high temperatures lasting for hours. Sodium carbonate, dissolved in water, tends to hardly release water at all as a result of hydrate formation. Therefore, the drying process requires a long period of time and high temperatures. With this preparation process one cannot rule out that yellow coloured granules are obtained. Concerning the amounts of water required for the preparation of ibuprofen granules for 100,000 tablets (cf. example 1 and 2 of EP-A-369 228) the enormous amount of 230 kg of water is calculated which has to be evaporated at 100° C.

As shown below according to the present invention, the preparation of the same amount of granules according to the present invention requires only 3.5 kg of water and 3 to 5 kg of ethanol. Therefore, the drying process is far more favourable in terms of economic efficiency as well as more careful.

EP-A-0 667 149 describes an ibuprofen effervescent tablet, in which potassium hydrogen carbonate (3 to 9 parts) should also be contained besides sodium hydrogen carbonate (3.5 to 12 parts), each based on 2 parts of ibuprofen. According to EP-A-0 667 149 not an effervescent couple is produced, but on the one hand the complete portion of bicarbonate is granulated together with the ingredient and on the other hand separate acid granules together with a sweetener and a sugar substitute are produced. However, there are also great doubts as to whether effervescent solutions are formed by this simple composition in which the active ingredient is completely dissolved within the usual time of a few minutes. All practical experiences have shown that dissolved ibuprofen in the form of its salt is again precipitated by the acid and rises to the water surface in the form of small oil droplets, gathers together and crystallizes gradually in form of coarse crystals which redissolve either not at all or only very slowly.

CH-A-684 929 describes ibuprofen-containing effervescent compositions. The ingredient is herein used in the form of the sodium- or potassium salt. The composition contains silica, which is insoluble and leads to a cloudy solution. However, this is undesired in case of analgetics; it is desired that the tablet dissolves to give a clear solution, as is already known regarding aspirin-effervescent tablets. The effervescent composition described in CH-A-684 929 contains further a cellulose ether and a surfactant in order to redissolve the precipitated ibuprofen in a better way. All in all, it can be taken from CH-A-684 929 that the precipitation of ibuprofen cannot be prevented und further measures have to be taken to achieve the redissolution of ibuprofen. The described ibuprofen-containing effervescent composition further contains nearly 1000 mg potassium- and sodium carbonate, leading to worse organoleptic properties.

EP-A-0 181 564 describes an effervescent ibuprofen formulation, wherein the ibuprofen particles are covered by a mucuos-producing compound such as xanthan and/or maltodextrin and fumaric acid and processed into granules. After milling of the granules, these granules are attached together with a further acid such as, for example, citric acid, onto sugar. These granules can also be admixed with an effervescent mixture made of citric acid and calcium carbonate. While dissolving the effervescent mixture of EP-A-0 181 564 in water, the active ingredient ibuprofen does not dissolve and forms a suspension in water. The ibuprofen particles can thus stick on the mucosa of mouth and pharynx and cause the commonly known irritations of mucosa when drinking this suspension.

The prices for analgetics are worldwide very low. The preparation of an active ingredient formulation in form of an effervescent tablet is still more expensive since the weight of the tablet has to be in the order of 3 g leading to high costs for packing material and high production costs. Therefore, it is our main concern to provide an effervescent tablet obtainable with favourable economic efficiency.

Therefore, it is the object of the present invention to provide a new ibuprofen effervescent formulation giving rise to a clearly dissolved active ingredient and a process for the preparation thereof.

This object is solved by the effervescent ibuprofen formulation containing two, separately produced granules:
(a) ibuprofen granules, prepared from ibuprofen acid and a basic adjuvant in a molar ratio of 1 mole of ibuprofen acid to 0.5–10 mole of basic adjuvant, and
(b) ibuprofen-free effervescent granules, containing an acid component and a carbon-dioxide generating component.

70% of the basic ibuprofen granules (a) are present in a grain size in the range of 0.1 and 2.0 mm, especially in the range of 0.1 to 1.25 mm. The effervescent ibuprofen formulation according to the present invention has a molar ratio of the ibuprofen acid to the acid component of the effervescent granules (b) in the range of 1 mole of ibuprofen acid to 0.5–6 mole of acid component. The molar ratio of the ibuprofen acid to the carbon dioxide generating component of the effervescent granules (b) is in the range of 1 mole of ibuprofen acid to 1–30 mole of the carbon dioxide generating component. It is an essential feature of the present invention that upon disintegration of the ibuprofen effervescent formulation, the effervescent granules (b) dissolve upon contact with water immediately to release (somewhat larger) ibuprofen granules (a), from which ibuprofen subsequently dissolves.

The invention further relates to the process for the preparation of an effervescent ibuprofen formulation characterized by preparing ibuprofen-containing granules (a) from ibuprofen acid and at least one basic adjuvant and optionally further water-soluble adjuvants; by separately preparing ibuprofen-free effervescent granules (b) containing an acid component and a carbon-dioxide generating component, mixing both components (a) and (b) together with conventional further adjuvants; compressing the effervescent formulation to effervescent tablets or filling the effervescent formulation into sachets.

Preferred embodiments of the invention are characterized in the dependent claims.

Surprisingly, it has been found that by very simple means the dissolving rate of the active ingredient ibuprofen acid and the great pH-dependance of the solubility thereof can be improved by combining the active ingredient with basic adjuvants. In particular, inorganic basic adjuvants such as sodium carbonate, potassium carbonate, sodium bicarbonate, potassium bicarbonate, basic phosphates such as trisodium phosphate are extremely suitable. All these adjuvants are characterized by extremely favourable prices and do not complicate in any way the preparation of granules which are further processed into effervescent tablets.

In a remarkably simple preparation according to this invention, ibuprofen acid is wetted in a wet-mixing apparatus by cheap basic adjuvants such as sodium carbonate, potassium carbonate, potassium hydrogen carbonate, sodium hydrogen carbonate, trisodium citrate, trisodium phosphate in a molar ratio of 0.5 to 10 moles of basic component, preferably 1.0 to 3 mole, for each mol of ibuprofen acid.

According to this invention, ibuprofen is present either as racemate, as racemic mixture of its enantiomers, as pseudoracemate, i.e. as a mixture of equal amounts of S- and R-ibuprofen or as mixture of different amounts of S- and R-ibuprofen ranging between pure S- and pure R-ibuprofen. A person skilled in the art knows that with respect to the S-form of ibuprofen only half of the amount for the racemate should be used, i.e. 100 to 200 mg in the case of effervescent tablets and 100 to 400 mg in case of effervescent granules.

The effervescent formulation according to the present invention is particularly present in the form of an effervescent tablet containing 200 to 800 mg racemic ibuprofen or 100 to 200 mg S-ibuprofen. In a preferred embodiment, the effervescent tablet according to the present invention contains 200 to 400 mg racemic ibuprofen. In another embodiment of the present invention, the effervescent formulation can be present in the form of granules filled in sachets containing 200 to 800 mg racemic ibuprofen or 100 to 400 mg S-ibuprofen. Preferably, the sachets contain 200 to 800 mg racemic ibuprofen.

After dissolving of 100 to 400 mg S-ibuprofen or 200 to 800 mg racemic ibuprofen, the pH-value is between 6.5 and 9.0, being equivalent to a corresponding amount of the effervescent formulation in 150 ml of water.

Suitable basic adjuvants according to this invention include particularly the following compounds from the group of $NaHCO_3$, $KHCO_3$, $Na_2CO_3$, $K_2CO_3$, $Na_3PO_4$, sodium citrate, $K_2O$, $Na_2O$, CaO, MgO, $Ca(OH)_2$, $Mg(OH)_2$ and basic magnesium carbonate, wherein $Na_2CO_3$, $K_2CO_3$, $Na_3PO_4$, $NaHCO_3$, $KHCO_3$ or mixtures thereof are particularly preferred.

Water or water-alcohol-mixtures such as water with ethanol and isopropanol can be used as wetting agents. In particular, mixtures of alcohol with water in the weight ratio of 2:8 to 8:2 are very suitable. Well-structured granules are formed also thereby without the addition of an adhesive. This simple granulation is more preferably carried out in a vacuum granulator wherein mixing, wetting and drying is carried out in the same apparatus. Formulations in the order of 500 kg can be sufficiently dried within 2 to 4 hours at a reaction vessel wall-temperature of 60° C. The granules are completely water soluble by the addition of the basic adjuvants. The generation of such a clear solution by such easily producable granules was totally surprising. The preparation of such granules is far cheaper than the use of ibuprofen-amino acid granules of arginine or lysine or ibuprofen sodium salts, respectively.

In addition to the active ingredient granules, the effervescent formulation according to this invention contains a separately produced effervescent couple. It is known that the dissolved ibuprofen is again easily neutralized by the acid of the effervescent couple leading to ibuprofen acid. This ibuprofen is unsoluble, rises in form of tiny oil droplets to the water surface by dissolution of the effervescent formulation and crystallizes in the form of coarse ibuprofen crystals which irritate the mucous membranes. This is avoided by two further steps according to this invention:

The acid necessary in each effervescent couple is directly and compactly combined with neutralizing, carbon dioxide generating $KHCO_3$, $NaHCO_3$ and sodium glycin carbonate. The resulting effervescent couple dissolves upon contact with water nearly spontaneously within a few seconds wherein the compounds $NaHCO_3$, $KHCO_3$ and sodium glycine carbonate, combined with the acid, instantly buffer the acid. The maximum dissolving rate of the effervescent couple in water at 20° C. is 60 seconds.

Ibuprofen is processed into well-structured, mechanically stable granules. At least 70% of the particles have a size between 0.1–1.25 mm, preferably 0.1–0.5 mm. The dissolving rate of the active ingredient granules is 50 seconds to 200 seconds in demineralized water at 20° C.

The two-step, sustained release-dissolution (i.e. time delayed) of both granules is essential for the invention. The main part of the acid is neutralized by the rapid dissolution of the effervescent couple before the ibuprofen dissolves. The two-step dissolution process of the effervescent formulation can clearly be seen by the addition thereof with water: by dissolution of the effervescent tablet, active ingredient granules drop out of the swimming tablet, sink to the bottom and dissolve clearly after a time-delay.

The sustained release-dissolution of the active ingredient granules can be controlled in various ways:

ratio of water/ethanol during the granulation kneading intensity during wetting sieve size during wet-sieving and dry-sieving of the granules.

Finally, solution-controlling, pharmaceutical widely-used, water soluble adjuvants such as lactose, mannite, sorbite, xylite, glycine, gelatine can be used during the granulation in addition to the active ingredient and the basic adjuvants. The basic adjuvants can also consist of mixtures in the cited molar ratio, such as, for example, of NaHCO3 or $Na_2CO_3$ or of $K_2CO_3$ and trisodium citrate.

The effervescent couple can be prepared by the usual components in the known manner. The acid component consists, for example, of citric acid, tartaric acid, malic acid, adipic acid, ascorbic acid and monosodium citrate. The latter is preferred. Preferably, sodium dihydrogencitrate is more particularly used. Also mixtures of the afore-mentioned components can be used. The carbon dioxide generating component consists of $NaHCO_3$, $KHCO_3$, $Na_2CO_3$, $K_2CO_3$ or sodium glycine carbonate, preferably $NaHCO_3$. The effervescent composition can contain further components such as xylite, sorbite, sodium sulphate and binders such as gelatine, polyvinylpyrrolidone and methylcellulose.

The effervescent formulation contains further adjuvants such as sweeteners and/or sugar exchangers and/or aromas.

Therefore, the effervescent formulation contains adjuvants such as sodium saccharine, sodium cyclamate, aspartam and dried-aromas. The formulation according to this invention is filled in bags or sachets as effervescent granules, or compressed to tablets having a weight of about 3–4 g, filled in tubes and sealed with a dry stopper.

The two-step dissolution of both granules according to this invention can excellently be checked in an in-vitro-releasing apparatus with a paddle mixer. The mentioned apparatus is described in detail in the European or German Pharmakopoe (DAB10).

Conditions:
  500 ml water, demineralized
  Temperature: 20° C.
  Rotation speed: 100 rpm
  Sample amount: 1 g active ingredient granules or effervescent couple granules
  Dissolution of effervescent couple granules: max. 60 seconds
  Dissolution of active ingredient granules: 50–200 seconds.

The granules according to this invention consist of ibuprofen acid and not of water soluble ibuprofen salt, Furthermore, the granules according to this invention do not contain any stabilizer.

It is expressly disclosed in EP-A-0 369 228 (Bayer) that ibuprofen in form of its water soluble salts is granulated together with an excipient and a stabilizer. Later an acid component is added to these basic granules.

According to this invention an effervescent couple is admixed to the granules. With respect to the granules according to this invention, PVP used in the effervescent couple clearly has the function of an adhesive for the effervescent couple and is not used to stabilize the dissolved ibuprofen, as expressly described in the Bayer patent.

In a more preferred embodiment of the invention, one mol of ibuprofen with 2.6 mole of sodium carbonate is granulated together with a mixture of water/ethanol 5:5. After drying and sieving well-structured granules having a granulometry essentially between 0.1 and 0.5 mm are formed. Less than 30% of these granules are <0.1 mm. The acid necessary for each effervescent tablet is mixed together with the carbon dioxide generating agent (sodium hydrogen carbonate or potassium hydrogen carbonate) in a separate granulation step. In particular, monosodium citrate is suitable as an acid component since it is less acidic than citric acid. Usually, binders such as for example polyvinylpyrrolidone (PVP) are used to prepare the effervescent couple. The granulation is preferably carried out with ethanol or isopropanol and a small addition of water. Further, structure-promoting adjuvants such as sorbite and xylite can be included. In addition to the active ingredient granules and the effervescent couple granules, sweeteners and aromas may also be added. As described in the examples, an effervescent tablet is obtained having a disintegration time between 1 and 2.5 minutes, having 200 mg ibuprofen and having the active ingredient in completely dissolved form after dissolving. By dissolving the effervescent tablet, a second step according to this invention occurs:

The effervescent tablet works in form of a two-step effervescent tablet, wherein the effervescent couple reacts very rapidly by addition of water, leading to the reaction between the acid and sodium hydrogen carbonate giving rise to strong carbon dioxide formation, wherein the acid is buffered by sodium hydrogen carbonate which is present in excess. It can be seen how granules consisting of ibuprofen and sodium carbonate drop out of the remaining effervescent tablet and only then dissolve in a second step. Therefore the following step according to this invention is achieved:

The acid is instantly buffered and neutralized by sodium hydrogen carbonate and cannot precipitate ibuprofen which is already dissolved. The release of ibuprofen as dissolved ibuprofen salt is delayed since the particles of the active ingredient granules dissolve much slower than the particles of the effervescent couple. Therefore, the ibuprofen substantially dissolves only after the acid has already been buffered by the bicarbonate. In this step of the invention the precipitation of dissolved ibuprofen by acid during the dissolution of the effervescent tablet can thus be prevented.

The ibuprofen granules consist essentially of the active ingredient and the aforementioned basic adjuvants. Readily water soluble adjuvants such as glycine, sorbite, mannite, saccharose, can be added to the active ingredient granules in an appropriate amount for controlling the active ingredient release, i.e. for dissolving the granules.

The invention is now described by the following examples in detail:

EXAMPLE 1

| a) Active ingredient granules | mg/dose | kg/100,000 applications |
|---|---|---|
| Ibuprofen | 200 mg | 20.0 kg |
| Potassium carbonate | 200 mg | 20.0 kg |
| Sodium hydrogen carbonate | 600 mg | 60.0 kg |

20.0 kg of ibuprofen, 20.0 kg of $K_2CO_3$ and 60.0 kg of $NaHCO_3$ were strongly mixed in a vacuum granulator and sprayed with a solution of 4 kg of water and 6 kg of ethanol under stirring. As soon as a clear structure had been formed, the reaction vessel was heated to 60° C. and the granules were dried for 2 hours. The dried granules were then sieved using a sieve having a mesh size of 1.0 mm. The granules obtained were enough for 100,000 applications.

| b) Effervescent couple | mg/dose | kg/100,000 applications |
|---|---|---|
| Sodium dihydrogen citrate | 700 mg | 70.0 kg |
| Sodium hydrogen carbonate | 1040 mg | 104.0 kg |
| Mannite | 200 mg | 20.0 kg |
| Polyvinylpyrrollidone | 20 mg | 2.0 kg |

The above-mentioned amounts of each listed component were mixed in a vacuum granulator and wetted with 16 kg of 90% ethanol. The granules were dried at 60° C. (temperature of the reaction vessel wall) for 1.5 hours and sieved using a sieve having a mesh size of 1.25 mm.

The dissolving rates were

Active ingredient granules: 108 seconds

Effervescent couple granules: 48 seconds.

Both granules were mixed, aspartam and aromas were added and the mixture was filled into bags. Each bag contained an amount of active ingredient granules corresponding to 200 mg ibuprofen.

A clear solution was formed after 2 minutes by dissolution in 150 ml water. The pH-value of the solution was 6.9.

EXAMPLE 2

| a) Active ingredient granules | mg/dose | kg/100,000 applications |
|---|---|---|
| Ibuprofen | 200 mg | 20.0 kg |
| $Na_2CO_3$ | 275 mg | 27.5 mg |
| Glycine | 200 mg | 20.0 kg |

As described in example 1, the three components were well mixed in a vacuum granulator and sprayed with a solution of 3.5 kg of water and 3.5 kg of ethanol. A marked structure of the granules was produced under strongly stirring.
Drying, cf. example 1
Dry sieving 1.00 mm, then 0.6 mm
Granulometry:
12% <0.1 mm
88% <0.6 mm.

| b) Effervescent couple | mg/dose | kg/100,000 applications |
|---|---|---|
| Sodium hydrogen carbonate | 1640 mg | 164.0 kg |
| Sodium dihydrogen citrate | 720 mg | 72.0 kg |
| Sorbite | 100 mg | 10.0 kg |
| Aspartam | 30 mg | 3.0 kg |
| Sodium saccharine | 10 mg | 1.0 kg |
| Polyvinylpyrollidone | 20 mg | 2.0 kg. |

As described in example 1, the mixed components were sprayed with 25 kg of 8% isopropanolic polyvinylpyrrolidone solution, then with 7.1 kg of a 70% sorbite solution. The granules were sieved through a 1.25 mm mesh size sieve after drying.

The dissolving rates are:
Effervescent couple granules: 50 seconds
Active ingredient granules: 130 seconds.

Both granules were mixed together with 5.5 kg of citric aroma and compressed to form effervescent tablets having a weight of 3.3 g.

The tablet decomposed within 95 seconds in 150 ml water at 20° C. and all components were clearly dissolved after 150 seconds. The pH-value was 7.0.

EXAMPLE 3

| a) Active ingredient granules | mg/dose | kg/100,000 applications |
|---|---|---|
| Ibuprofen | 800 mg | 80.0 kg |
| $Na_2CO_3$ | 210 mg | 21.0 kg |

As described in example 1, the two components were well mixed in a vacuum granulator and sprayed with a solution of 7 kg of water and 3 kg of isopropanol. A marked structure of the granules was formed by strong stirring.
Drying, cf. example 1.
Dry sieving: 1.00 mm
Granulometry:
27% <0.1 mm
73% <1.0 mm.

| b) Effervescent couple | mg/dose | kg/100,000 applications |
|---|---|---|
| Sodium hydrogen carbonate | 1000 mg | |
| Citric acid | 400 mg | 100.0 kg |
| Saccharose | 2000 mg | 200.0 kg |
| Sodium saccharine | 15 mg | 1.5 kg |
| Sorbite | 85 mg | 8.5 kg |

As described in example 1, the mixed components were wetted with 25 kg of isopropanol and then with 11.3 kg of an aqueous 75% sorbite solution.

The granules were sieved through a 0.71 mm mesh size sieve after drying.
The dissolving rates were:
Active ingredient granules: 154 seconds
Effervescent couple granules: 58 seconds.

Both granules were mixed, peppermint aroma was added and the mixture was filled into bags. Each bag contained an amount of the granules corresponding to 800 mg ibuprofen. A clear solution was formed after 3 minutes by dissolution in 200 ml water. However, bags can also be filled to contain 200, 400, 600 mg ibuprofen by maintaining the described amount of the effervescent couple.

Comparative Example 1 (according to EP-A-369 228; example 2)

Example 2 of EP-A-369 228 has been repeated in exactly the same way.

Ibuprofen-effervescent granules, with which 200 mg ibuprofen is administered, is composed of:

| | |
|---|---|
| 1) Ibuprofen-sodium salt | 0.443 kg |
| 2) Polyvinylpyrrolidone | 0.160 kg |
| 3) Sodium hydrogen carbonate | 2.700 kg |
| 4) Water | 1.565 kg |

Batch size: 2000 effervescent tablets.

The solution is prepared from the components 1), 2) and 4), which is sprayed onto the sodium hydrogen carbonate present in a fluid system apparatus.

Temperature: 90° C.
Spray pressure: 1.2 bar
Spray time: 30 min.

Well structured granules are obtained. The granules are sprayed with a solution of
sodium carbonate 0.300 kg and
water 1.675 kg
under the same conditions as above.

The spray time takes 32 minutes.

After drying for a short period of time the granules are sprayed with a solution of
disodium fumarate 0.300 kg and
water 2.000 kg
under the same conditions as above.

The spraying time was 38 minutes.

Drying takes 4 hours at 55° C. in a circulation heat box.
The granules are white, well structured and well flowable. The drying loss at 70 ° C. is below 1%.

The preparation of tablets is carried out using
1.951 kg granules and
0.549 kg citric acid.

Both components were mixed together for 20 minutes. This mixture is compressed to tablets having a diameter of 25 mm and a breaking strength of 60–90 N.

Test Results

The tablets according to EP-A-0 369 228 decompose in 100 ml water at 20° C. within 2 to 3.5 minutes with severe precipitation of ibuprofen. The oily precipitated, semi-cristalline ibuprofen gathers together on the water surface in form of a foam and deposits on the wall of the glass as a semi-cristalline white rim. If this cloudy solution with the precipitated ibuprofen is drunk, the known, absolutely intolerable burning of undissolved ibuprofen acid occurs on the mucous membranes of the oral cavity. If the solution is stirred for 6–8 minutes, the precipitated ibuprofen is dissolved. A clear solution having a pH-value of 6.8 is obtained.
Evaluation:

Admittedly, the effervescent tablet decomposes in about 2–3.5 minutes. However, a cloudy solution is obtained, on which surface great amounts of precipitated ibuprofen are present. This suspension is not drinkable. A dissolution of the precipitated ibuprofen by stirring for 6–8 minutes is not tolerable. Effervescent tablets should dissolve clearly or almost clearly within about 3 minutes.

Although the granules dissolve totally clearly before the addition of citric acid, the addition of citric acid leads to a spontaneous, obviously unavoidable precipitation of the ibuprofen already dissolved.

Comparative example 2 (according to EP-A-0 667 149; example 1)

Example 1 of EP-A-667 149 has been repeated in-exactly the same way:

According to the preparation described in example 1 of EP-A-667 149, basic granules having the following composition are prepared (batch size 2000 tablets)

| | |
|---|---|
| 1) Ibuprofen | 0.400 kg |
| 2) Sodium hydrogen carbonate | 1.000 kg |
| 3) Potassium hydrogen carbonate | 1.400 kg |
| 4) Sucrose monopalmitate | 0.005 kg |
| 5) Water | 1.000 kg |

In exact accordance with example 1 of EP-A-667 149, a solution is prepared from the components 4) and 5), which is sprayed onto the sieved mixture of the components 1), 2) and 3), present in a fluid system apparatus.

Temperature: 60° C.

Spray pressure: 1.0 bar

Spray time: 15 minutes

Drying: 20 minutes

Drying loss: 0.6% at 70° C.

The granules are well structured and flowable and dissolve clearly in demineralized water.

Under the described conditions the citric acid 1.080 kg is separately granulated with the aqueous solution of aspartam and 0.140 kg sorbit 0.400 kg and dried.

Drying loss: 0.3% at 70° C.

The two types of granules, sieved through 1.0 mm, were mixed together with 67 g dried orange-aroma according to example 1 and compressed to 2.5 g heavy effervescent tablets. Breaking strength 60–80 N.
Result:

The tablets decompose in 150 ml water at 16–18° C. within 2–2.5 minutes with severe precipitation of ibuprofen. A sticky, gluey layer of precipitated, cristalline or semi-cristalline ibuprofen acid is formed on the water surface. If the cristalline suspension is drunk after disintegration of the tablet, the known, very unpleasant burning on the mucous membranes of the oral cavity occurs, caused by the undissolved ibuprofen acid. If the cristalline suspension is stirred for about 7 minutes, a clear solution having a pH-value of 7.1–7.3 is obtained.
Evaluation:

The effervescent tablet decomposes within about 2–3.5 minutes as indicated. A clear solution is obtained, however, having a considerable, untolerable amount of precipitated ibuprofen acid, which swims on the water surface. This cristalline suspension is not drinkable.

A dissolution of the precipitated ibuprofen acid by stirring after about 7 minutes is not acceptable.

Although the granules dissolve totally clearly before the addition of citric acid, the addition of citric acid leads to a spontaneous, obviously unavoidable precipitation of ibuprofen already dissolved.

In summary, it is shown from the comparative examples that a clear, drinkable ibuprofen solution can be obtained only with the help of the effervescent formulation according to the present invention. With the help of the measures according to the present invention, it was therefore possible for the first time, to remove the acid effect of the citric acid contained in the effervescent couple by the following measures among other things.

The citric acid has to be mixed directly with the base sodium hydrogen carbonate, and seperat effervescent couple granules have to be prepared therefrom.

The sodium dicarbonate has to buffer the main part of the citric acid within the dissolution of the effervescent couple granules, before great amounts of ibuprofen from the ingredient granules dissolve, i.e. according to the present invention sustained relief-dissolving ibuprofen-granules and rapidly dissolving effervescent couples-granules are provided.

What is claimed is:

1. An effervescent ibuprofen formulation containing two, separately produced granules:

(a) ibuprofen granules, prepared from ibuprofen acid and a basic adjuvant in a molar ratio of 1 mole of ibuprofen acid to 0.5–10 mole of basic adjuvant, wherein at least 70% of the basic ibuprofen granules (a) are present in a grain size in the range of 0.1 and 2.0 mm, and (b) ibuprofen-free effervescent granules, containing an acid component and a carbon-dioxide generating component, wherein said effervescent formulation has a molar ratio of the ibuprofen acid to the acid component of the effervescent granules (b) in the range of 1 mole of ibuprofen acid to 0.5–6 mole of acid component and the molar ratio of the ibuprofen acid to the carbon dioxide generating component of the effervescent granules (b) is in the range of 1 mole of ibuprofen acid to 1–30 mole of the carbon dioxide generating component, and wherein upon disintegration of the ibuprofen effervescent formulation, the effervescent granules (b) dissolve upon contact with water immediately to release ibuprofen granules (a), from which ibuprofen subsequently dissolves.

2. Effervescent formulation according to claim 1 in which the ibuprofen acid is present as a racemate, as a racemic mixture of it enantiomers, as a pseudo-racemate, as mixtures of the equal amounts of S- and R-ibuprofen, or as mixtures of different amounts of S- and R-ibuprofen ranging between pure S- and pure R-ibuprofen.

3. Effervescent formulation according to claim 1 in which the ibuprofen-containing granules (a) contain at least one basic adjuvant selected from the group consisting of sodium carbonate, potassium carbonate, sodium bicarbonate, potassium bicarbonate, calcium oxide, calcium hydroxide, magnesium oxide, magnesium hydroxide, magnesium carbonate, trisodium phosphate, tripotassium phosphate and mixtures thereof.

4. Effervescent formulation according to claim 1 in which the basic adjuvant is sodium carbonate and/or potassium carbonate.

5. Effervescent formulation according to claim 1, in which the acid component of the effervescent granules (b) is at least one selected from the group consisting of tartaric acid, citric acid, ascorbic acid, malic acid, adipic acid, sodium dihydrogencitrate and mixtures thereof.

6. Effervescent formulation according to claim 5 in which the acid component is sodium dihydrogencitrate.

7. Effervescent formulation according to claim 1 in which the carbon-dioxide generating component is selected from the group consisting of sodium bicarbonate, sodium carbonate, potassium bicarbonate, potassium carbonate, sodium glycine carbonate and mixtures thereof.

8. Effervescent formulation according to claim 7 in which the carbon dioxide generating component is sodium bicarbonate and/or potassium bicarbonate.

9. Effervescent formulation according to claim 2 in the form of effervescent tablets which is characterized by containing 200 to 800 mg of racemic ibuprofen or 100 to 400 mg of S-ibuprofen.

10. Effervescent formulation according to claim 9 in which the effervescent tablet contains 200 to 400 mg of racemic ibuprofen.

11. Effervescent formulation according to claim 2 in the form of granules filled into sachets which contain 200 to 800 mg of racemic ibuprofen or 100 to 400 mg of S-ibuprofen.

12. Effervescent formulation according to claim 11 in which the sachets contain 200 to 800 mg of racemic ibuprofen.

13. Effervescent formulation according to claim 1 in which at least 70% of the basic ibuprofen granules (a) have a grain size in the range of between 0.1 and 1.25 mm.

14. Effervescent formulation according to claim 1 in which the ibuprofen granules (a) have a dissolving rate from 50 to 200 sec.

15. Effervescent formulation according to claim 1 in which a pH-value of between 6.5 and 9.0 is obtained after dissolving an amount of the effervescent formulation corresponding to 100–400 mg of S-ibuprofen or 200–800 mg of racemic ibuprofen in 150 ml water.

16. Effervescent formulation according to claim 1 in which the ibuprofen granules (a) further contain known adjuvants for controlling the dissolving rate.

17. Effervescent formulation according to claim 1 which further contains adjuvants selected from the group consisting of sweeteners, sugar exchangers and fragrances.

18. Process for the preparation of an effervescent ibuprofen formulation according to claim 1 characterized by preparing ibuprofen-containing granules (a) from ibuprofen acid and at least one basic adjuvant and optionally further water-soluble adjuvants; by separately preparing ibuprofen-free effervescent granules (b) containing an acid component and a carbon-dioxide generating component; mixing both components (a) and (b) together with conventional further adjuvants; compressing the effervescent formulation to effervescent tablets or filling the effervescent formulation into sachets.

19. Effervescent formulation according to claim 2 in which the basic adjuvant is sodium carbonate and/or potassium carbonate.

20. Effervescent formulation according to claim 3 in which the basic adjuvant is sodium carbonate and/or potassium carbonate.

* * * * *